US011589755B2

(12) United States Patent
Kang et al.

(10) Patent No.: US 11,589,755 B2
(45) Date of Patent: Feb. 28, 2023

(54) APPARATUS AND METHOD FOR ESTIMATING BIO-INFORMATION

(71) Applicant: SAMSUNG ELECTRONICS CO., LTD., Suwon-si (KR)

(72) Inventors: Jae Min Kang, Seoul (KR); Yong Joo Kwon, Yongin-si (KR); Youn Ho Kim, Hwaseong-si (KR); Sang Yun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 812 days.

(21) Appl. No.: 16/415,586

(22) Filed: May 17, 2019

(65) Prior Publication Data

US 2020/0085315 A1 Mar. 19, 2020

(30) Foreign Application Priority Data

Sep. 18, 2018 (KR) ........................ 10-2018-0111282

(51) Int. Cl.
A61B 5/0205 (2006.01)
A61B 5/02 (2006.01)
A61B 5/16 (2006.01)
A61B 5/00 (2006.01)
A61B 5/021 (2006.01)

(52) U.S. Cl.
CPC ........ *A61B 5/0205* (2013.01); *A61B 5/02007* (2013.01); *A61B 5/165* (2013.01); *A61B 5/442* (2013.01); *A61B 5/6843* (2013.01); *A61B 5/02116* (2013.01)

(58) Field of Classification Search
None
See application file for complete search history.

(56) References Cited

U.S. PATENT DOCUMENTS

| 10,931,859 | B2 * | 2/2021 | Bhat ................... A61B 5/1172 |
| 2015/0062078 | A1 * | 3/2015 | Christman .......... A61B 5/6897 345/174 |
| 2016/0278645 | A1 | 9/2016 | Yoon |

(Continued)

FOREIGN PATENT DOCUMENTS

| EP | 3 342 336 A1 | 7/2018 |
| KR | 10-0660349 B1 | 12/2006 |

(Continued)

OTHER PUBLICATIONS

Nam, Yunyoung et al., "Photoplethysmography Signal Analysis for Optimal Region-of-Interest Determination in Video Imaging on a Built-in Smartphone under Different Conditions", sensors, Oct. 17, 2017, vol. 17, No. 2385, pp. 1-18. (18 pages total).

(Continued)

*Primary Examiner* — Yi-Shan Yang
(74) *Attorney, Agent, or Firm* — Sughrue Mion, PLLC

(57) ABSTRACT

An apparatus for estimating bio-information includes: a sensor part configured to obtain contact pressure of a contact surface contacted by an object, and configured to obtain a contact image of the object that contacts the contact surface; and a processor configured to obtain a pulse wave signal of a region of interest based on the contact image, and configured to estimate bio-information based on the obtained pulse wave signal and the contact pressure.

17 Claims, 15 Drawing Sheets

(56) References Cited

U.S. PATENT DOCUMENTS

| | | | |
|---|---|---|---|
| 2017/0119307 A1 | 5/2017 | Shim et al. | |
| 2017/0185234 A1 | 6/2017 | Zhang | |
| 2017/0255812 A1 | 9/2017 | Kwon | |
| 2018/0177413 A1 | 6/2018 | Kwon et al. | |
| 2018/0358119 A1* | 12/2018 | Bhushan | G16H 40/63 |

FOREIGN PATENT DOCUMENTS

| | | | |
|---|---|---|---|
| KR | 10-2015-0082045 A | 7/2015 | |
| KR | 10-2016-0115017 A | 10/2016 | |
| KR | 10-2017-0103558 A | 9/2017 | |
| WO | 2017/074713 A1 | 5/2017 | |

OTHER PUBLICATIONS

Sun, Yu et al., "Photoplethysmography Revisited: From Contact to Noncontact, From Point to Imaging", IEEE Transactions on Biomedical Engineering, Sep. 24, 2015, vol. 00, No. 0, pp. 1-15. (16 pages total).

Communication dated Jan. 21, 2020 issued by the European Patent Office in counterpart European Patent Application No. 19185409.0.

\* cited by examiner (1)　　(2)

APPARATUS AND METHOD FOR ESTIMATING BIO-INFORMATION

CROSS-REFERENCE TO RELATED APPLICATION(S)

This application claims priority from Korean Patent Application No. 10-2018-0111282, filed on Sep. 18, 2018, in the Korean Intellectual Property Office, the entire disclosure of which is incorporated herein by reference for all purposes.

BACKGROUND

1. Field

Apparatuses and methods consistent with example embodiments relate to apparatuses and methods for estimating bio-information, and more particularly, to technology for estimating blood pressure in a cuffless manner.

2. Description of the Related Art

Among methods of measuring blood pressure in a non-invasive manner without damaging a human body, a cuff-based measurement method may be used to measure blood pressure using cuff pressure measurements and a cuffless measurement method may be used to estimate blood pressure using pulse wave measurements without a cuff.

The cuff-based measurement method for measuring blood pressure includes a Korotkoff-sound method which measures blood pressure by winding a cuff around an upper arm and hearing the sound of blood vessels through a stethoscope during inflation and deflation of the cuff; and an Oscillometric method which measures blood pressure by winding a cuff around an upper arm and continuously measuring cuff pressure while inflating and then gradually deflating the cuff using an automated device, and measuring blood pressure based on a point having a maximum change of pressure signal.

The cuffless measurement method for measuring blood pressure includes a method of estimating blood pressure by calculating a Pulse Transit Time (PTT), and a Pulse Wave Analysis (PWA) method of estimating blood pressure by analyzing a pulse wave form.

SUMMARY

According to an aspect of an example embodiment, there is provided an apparatus for estimating bio-information, the apparatus including: a sensor part including a contact pressure sensor array configured to obtain a contact pressure distribution of a contact surface contacted by an object, and an image sensor configured to obtain a contact image of the object that contacts the contact surface; and a processor configured to obtain a pulse wave signal of a region of interest based on the contact image, and configured to estimate bio-information based on the obtained pulse wave signal and the contact pressure distribution.

The sensor part may further include a display panel between the contact pressure sensor array and the image sensor.

The image sensor may detect light which is emitted from the display panel and is reflected or scattered from the object.

The contact pressure sensor array may include a light-transmitting material.

The processor may divide the contact image into one or more regions, and select the region of interest based on at least one of a region including a characteristic point in the contact image, and a quality of a pulse wave signal of each of the one or more regions.

The characteristic point may include a fingerprint center point of a finger.

The processor may evaluate the quality of the pulse wave signal based on at least one of a maximum amplitude value of the pulse wave signal of each of the one or more regions, a difference between the maximum amplitude value and a minimum amplitude value of the pulse wave signal of each of the one or more regions, and an average amplitude value of the pulse wave signal of each of the one or more regions.

The processor may obtain at least one of a total sum, a mean value, a median value, a maximum value, and a minimum value of image data in each of the one or more regions at each measurement time, and a value calculated by applying a pre-defined function to the image data in each of the one or more regions at each measurement time, as an amplitude component of the pulse wave signal of each of the one or more regions.

The processor may divide the contact image into one or more regions, and select the region of interest based on a contact pressure at a position corresponding to each of the one or more regions in the contact pressure distribution.

The processor may estimate the bio-information based on contact pressure at a position corresponding to the region of interest in the contact pressure distribution, and the pulse wave signal of the region of interest.

The processor may obtain an oscillometric envelope based on the contact pressure and the pulse wave signal of the region of interest, obtain at least one feature value based on the oscillometric envelope, and estimate the bio-information by using the at least one feature value, the oscillometric envelope representing a contact pressure versus an amplitude of the pulse wave signal of the region of interest at each measurement time.

The at least one feature value may include one or more of a first contact pressure value of a maximum amplitude point, a second contact pressure value located to a left of the first contact pressure value, and a third contact pressure value located to a right of the first contact pressure value, the second contact pressure value and the third contact pressure value having a predetermined ratio to the first contact pressure value of the maximum amplitude point, in the oscillometric envelope.

The processor may determine a contact state between the object and the sensor part based on at least one of the contact pressure distribution, the contact image, and the pulse wave signal of the region of interest.

The apparatus may further include an output part configured to output information on the contact state.

The bio-information may include one or more of blood pressure, vascular age, arterial stiffness, aortic pressure waveform, vascular compliance, stress index, degree of fatigue, skin elasticity, and skin age.

According to an aspect of an example embodiment, there is provided a method of estimating bio-information, the method including: obtaining a contact pressure distribution of a contact surface contacted by an object; obtaining a contact image of the object that contacts the contact surface; obtaining a pulse wave signal of a region of interest based on the contact image; and estimating bio-information based on the obtained pulse wave signal and the contact pressure distribution.

The obtaining the pulse wave signal of the region of interest may include: dividing the contact image into one or more regions; and selecting the region of interest based on at least one of a region including a characteristic point in the contact image, and quality of a pulse wave signal of each of the one or more regions.

The selecting may include evaluating the quality of the pulse wave signal of each of the one or more regions based on at least one of a maximum amplitude value of the pulse wave signal of each of the one or more regions, a difference between the maximum amplitude value and a minimum amplitude value of the pulse wave signal of each of the one or more regions, and an average amplitude value of the pulse wave signal of each of the one or more regions.

The obtaining the pulse wave signal of the region of interest may include: dividing the contact image into one or more regions; and selecting the region of interest based on contact pressure at a position corresponding to each of the one or more regions in the contact pressure distribution.

The estimating may include estimating the bio-information based on the contact pressure at a position corresponding to the region of interest in the contact pressure distribution, and the pulse wave signal of the region of interest.

The estimating the bio-information based on the contact pressure and the pulse wave signal may include: obtaining an oscillometric envelope, which represents a contact pressure versus an amplitude of the pulse wave signal of the region of interest at each measurement time, based on the contact pressure and the pulse wave signal of the region of interest; obtaining at least one feature value based on the oscillometric envelope; and estimating the bio-information by using the at least one feature value.

According to an aspect of an example embodiment, there is provided an apparatus for estimating bio-information, the apparatus including: a sensor part including an image sensor configured to obtain a contact image of an object that contacts a contact surface, and a force sensor configured to detect a contact force applied by the object that contacts the contact surface; and a processor configured to obtain a pulse wave signal of a region of interest and a contact area of the object based on the contact image, and configured to estimate bio-information based on the contact area, the contact force, and the pulse wave signal.

The sensor part may further include a display panel which is disposed on the image sensor and is contacted by the object.

The image sensor may detect light which is emitted from the display panel and is reflected or scattered from the object.

The processor may divide the contact image into one or more regions, and select the region of interest based on at least one of a region including a characteristic point in the contact image, and a quality of a pulse wave signal quality of each of the one or more regions.

The processor may obtain contact pressure based on the contact force and the contact area, and estimate the bio-information using oscillometry based on the obtained contact pressure and the pulse wave signal.

According to an aspect of an example embodiment, there is provided a method of estimating bio-information, the method including: detecting a contact force applied by an object that contacts a contact surface; obtaining a contact image of the object that contacts the contact surface; obtaining a pulse wave signal of a region of interest and a contact area of the object based on the contact image; and estimating bio-information based on the contact area, the contact force, and the pulse wave signal.

The obtaining the pulse wave signal of the region of interest may include: dividing the contact image into one or more regions; and selecting the region of interest based on at least one of a region including a characteristic point in the contact image, and a quality of a pulse wave signal of each of the one or more regions.

The estimating the bio-information may include: obtaining contact pressure based on the contact force and the contact area; and estimating the bio-information based on the obtained contact pressure and the pulse wave signal of the region of interest.

BRIEF DESCRIPTION OF THE DRAWINGS

The above and/or other aspects will be more apparent by describing certain example embodiments with reference to the accompanying drawings, in which.

DETAILED DESCRIPTION

Figure 1A:
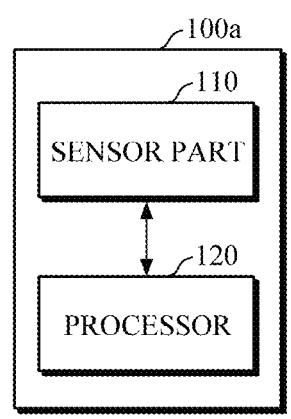
FIGS. 1A and 1B are block diagrams illustrating an apparatus for estimating bio-information according to example embodiments.

Details of example embodiments are included in the following detailed description and drawings. Aspects of example embodiments will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of an apparatus and a method of estimating bio-information will be described in detail with reference to the accompanying drawings. Various embodiments of the bio-information estimating apparatus may be applied to various devices, such as a portable wearable device, a smart device, and the like. Examples of the various devices may include, but are not limited to, a wearable device of various types such as a smart watch worn on the wrist, a smart band-type wearable device, a headphone-type wearable device, a hairband-type wearable device, and the like, a mobile device such as a smartphone, a tablet personal computer (PC), and the like.

Figure 1B:
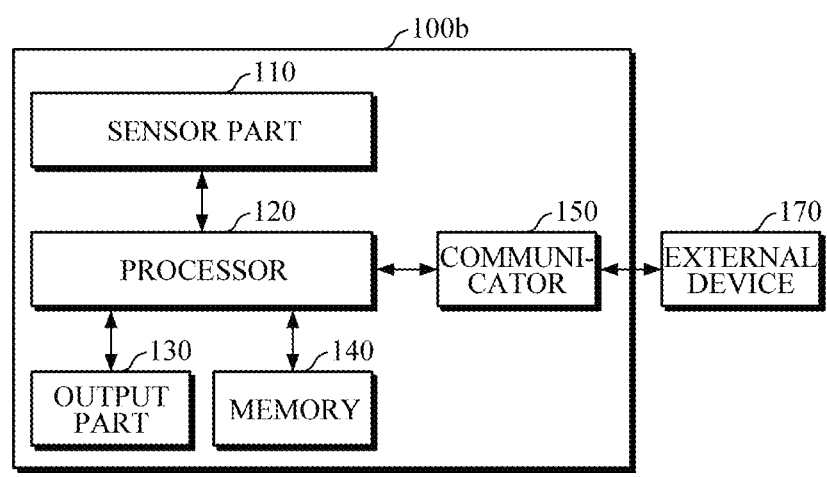
Figure 2A:
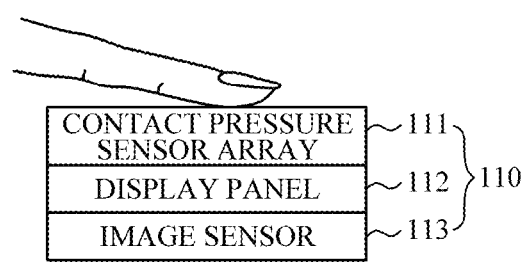
FIGS. 2A to 2B are diagrams illustrating structures of a sensor part according to example embodiments.
Figure 2B:
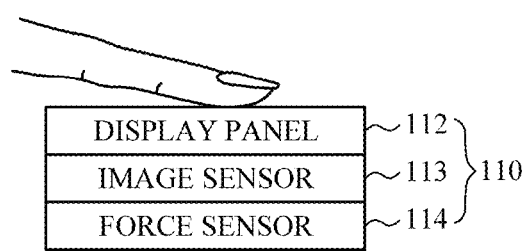

FIGS. 1A and 1B are block diagrams illustrating an apparatus for estimating bio-information according to example embodiments. FIGS. 2A to 2B are diagrams illustrating structures of a sensor part according to example embodiments.

Referring to FIGS. 1A and 1B, the bio-information estimating apparatuses 100a and 100b include a sensor part 110 and a processor 120.

Referring to FIG. 2A, the sensor part 110 includes a contact pressure sensor array 111, a display panel 112, and an image sensor 113.

The contact pressure sensor array 111 may be provided as an array of a plurality of contact pressure sensors which are arranged in predetermined various shapes. In an example embodiment, the predetermined shape in which the plurality of contact pressure sensors are arranged may be a two-dimensional matrix which is square-shaped, but is not limited thereto. For example, the plurality of contact pressure sensors may be arranged in a circular shape, an oval shape, a cross shape, or may be arranged by considering characteristics of an object. Each of the plurality of contact pressure sensors included in the contact pressure sensor array 111 may be a force sensor having a unit area size. When an object is in contact with a contact surface and gradually changes a contact intensity applied to the contact surface, the contact pressure sensor array 111 may obtain contact pressure distribution of the contact surface at each measurement time, and thus may obtain a change in the contact pressure distribution during an entire measurement time period.

The display panel 112 may include a touch screen which receives a touch input of a user, transmits the received touch input to the processor 120, and displays a processing result of the processor 120. In addition, at least a portion of light emitted from the display panel 112 may be used as a light source for detecting a pulse wave signal from an object. For example, light emitted from the display panel 112 may be incident onto an object when the object contacts the contact surface of the contact pressure sensor array 111. The display panel 112 may include, for example but is not limited to, a liquid crystal display (LCD) panel, a thin film transistor-LCD (TFT-LCD) panel, an organic light-emitting diode (OLED) display panel, a flexible display panel, a three-dimensional (3D) display panel, and a transparent organic light-emitting diode (TOLED) display panel. The display panel 112 may be implemented using any commonly known technology, and detailed description thereof will be omitted.

The image sensor 113 may obtain a contact image when the object contacts the contact surface of the contact pressure sensor array 111. In this case, the contact image includes a still image and/or a moving image. The contact image is not specifically limited to either one of the still image and the moving image. The image sensor 113 may be an optical image sensor, e.g., Complementary Metal Oxide Semiconductor (CMOS) Image Sensor (CIS) and/or a fingerprint sensor. However, the image sensor 113 is not limited thereto. The image sensor 113 may include a pixel array, and each pixel of the pixel array may include a detector, such as a photo diode or a photo transistor, which detects light and converts the detected light into an electric signal. For example, when light emitted from the display panel 112 is incident onto the object and then is reflected or scattered from the object, each pixel of the image sensor 110 may detect the reflected or scattered light, may convert the detected light into an electric signal, and may output the signal as image data.

As illustrated in FIG. 2A, the sensor part 110 may include the contact pressure sensor array 111, the display panel 112, and the image sensor 113 which are arranged in a multi-layer structure. The contact pressure sensor array 111 may be disposed at the top and has a contact surface to be touched by an object. Further, the contact pressure sensor array 111 and the display panel 112 may include a transparent material so that light emitted from the display panel 112 and reflected from the object may be transmitted therethrough. The image sensor 113 may be disposed at the bottom of the structure. A filter array may be interposed between the image sensor 113 and the display panel 112, and may include a color filter which is disposed at the top of each pixel of the image sensor 113 to transmit r block light in a specific spectrum region. For example, a microlens for improving light collection may be disposed at the top of each pixel of the image sensor 113.

Referring to FIG. 2B, the sensor part 110 includes the display panel 112, the image sensor 113, and a force sensor 114.

As illustrated in FIG. 2B, the sensor part 110 may be provided in a multi-layer structure. The display panel 112 may be disposed at the top with a contact surface to be touched by an object. As described above, the display panel 112 may serve as a light source for detecting a pulse wave signal from an object, and the image sensor 113 may obtain a contact image of the object by detecting light reflected or scattered from the object. In addition, the image sensor 113 may include an area sensor configured to detect a contact area of the object.

As illustrated in FIG. 2B, the force sensor 114 may be disposed at the bottom of the sensor part 110. The force sensor 114 may detect a change in the contact force applied by the finger to the contact surface in response to detecting that an object, e.g., a finger, presses the contact surface of the display panel 112 with gradually increasing force for a predetermined period of time, or in response to detecting that the object presses the contact surface with a pressure greater than or equal to a predetermined threshold and then presses the contact surface with gradually decreasing force.

The processor 120 may be electrically connected to the sensor part 110, and may control the sensor part 110 in response to a request for estimating bio-information. The processor 120 may receive data detected or obtained by the sensor part 110, and may estimate bio-information based on the received data. In this case, the bio-information may include one or more of blood pressure, vascular age, arterial stiffness, aortic pressure waveform, vascular compliance, stress index, degree of fatigue, skin elasticity, and skin age.

Figure 3:
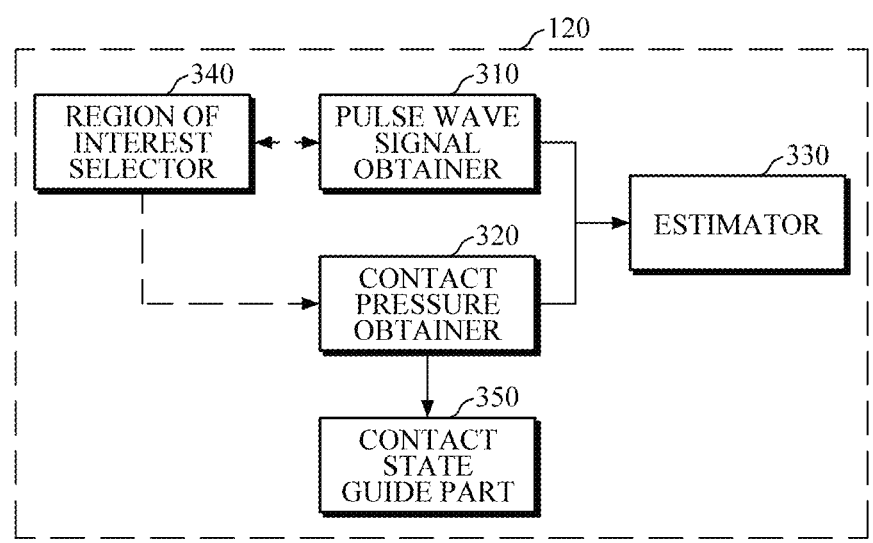
FIG. 3 is a block diagram illustrating a processor according to an example embodiment.

FIG. 3 is a block diagram illustrating a processor according to an example embodiment. FIGS. 4A to 4F are diagrams explaining an example of selecting a region of interest and estimating bio-information according to example embodiments. Hereinafter, an example of a processor 120 will be described with reference to FIGS. 1 to 4F.

Referring to FIG. 3, the processor 120 includes a pulse wave signal obtainer 310, a contact pressure obtainer 320, an estimator 330, a region of interest selector 340, and a contact state guide part 350.

The pulse wave signal obtainer 310 may obtain a pulse wave signal of a region of interest based on contact image data received from the image sensor 113 of the sensor part 110. The pulse wave signal obtainer 310 may obtain a pulse wave signal from each of one or more regions divided from a contact image. The pulse wave signal obtainer 310 may obtain a pulse wave signal from each region of the contact image by using the contact image data, e.g., pixel values output from each pixel of the image sensor 113. For example, the pulse wave signal obtainer 310 may obtain a total sum, a mean value, a maximum value, and/or a minimum value of pixel values or a value calculated using a pre-defined function of pixel values in any one of regions of the contact image that are obtained at any given time, and determine the obtained value as an amplitude component of the pulse wave signal for the corresponding region at the given time. In this manner, the pulse wave signal obtainer 310 may obtain amplitude components for the region at all of time points, to obtain pulse wave signals during the entire measurement time period.

Figure 4A:
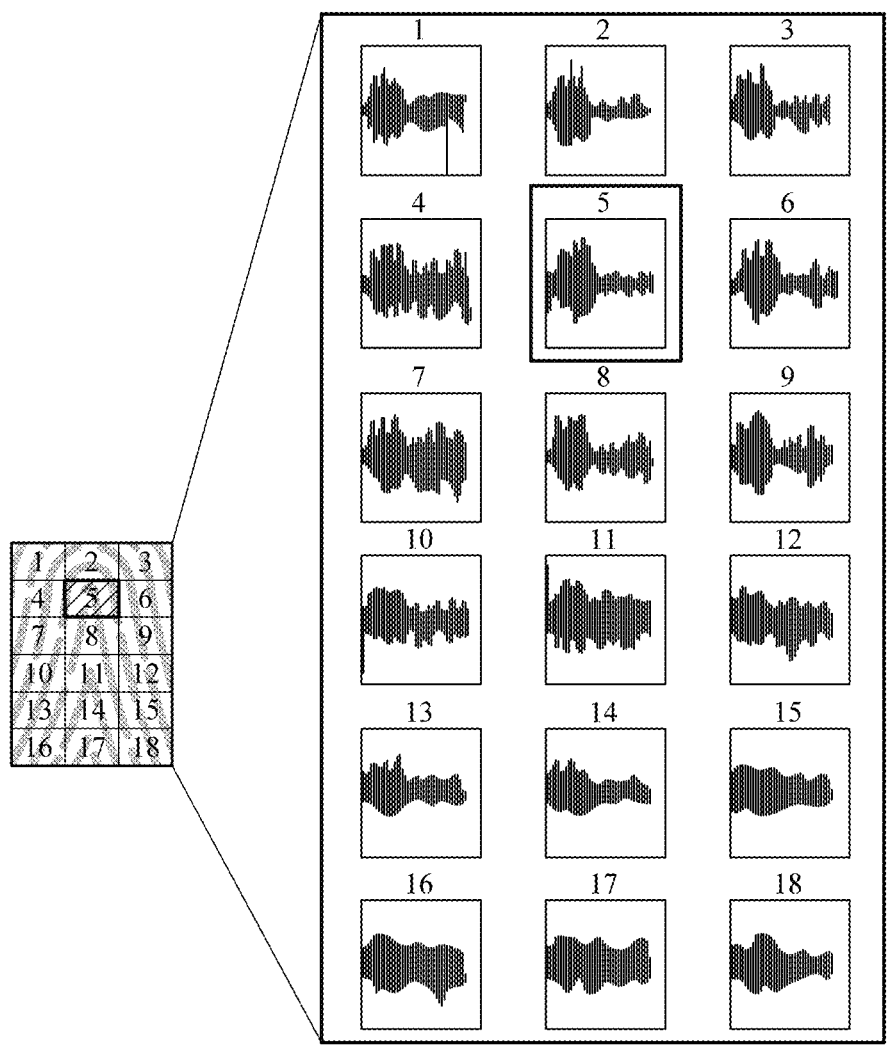
FIGS. 4A to 4F are diagrams explaining an example of selecting a region of interest and estimating bio-information according to example embodiments.

Among the obtained pulse wave signals of each region, the pulse wave signal obtainer 310 may select a pulse wave signal of a region of interest, selected by the region of interest selector 340, as a pulse wave signal for estimating bio-information. For example, FIG. 4A illustrates an example embodiment where the pulse wave signal obtainer 310 obtains pulse wave signals in 18 regions of a contact image. Here, a pulse wave signal of a fifth region of the contact image, which is selected as a region of interest, may be input into the estimator 330 for estimating bio-information. In the case where a region of interest is pre-selected by the region of interest selector 340, the pulse wave signal obtainer 310 may directly obtain a pulse wave signal of the region of interest without need to obtain pulse wave signals of other regions.

The contact pressure obtainer 320 may obtain contact pressure for estimating bio-information by using data received from the sensor part 110.

Figure 4B:
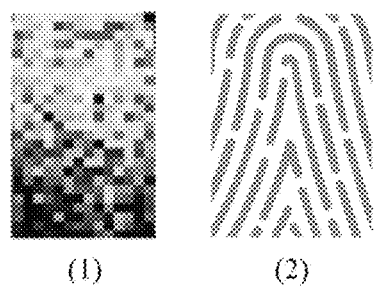
Figure 4C:
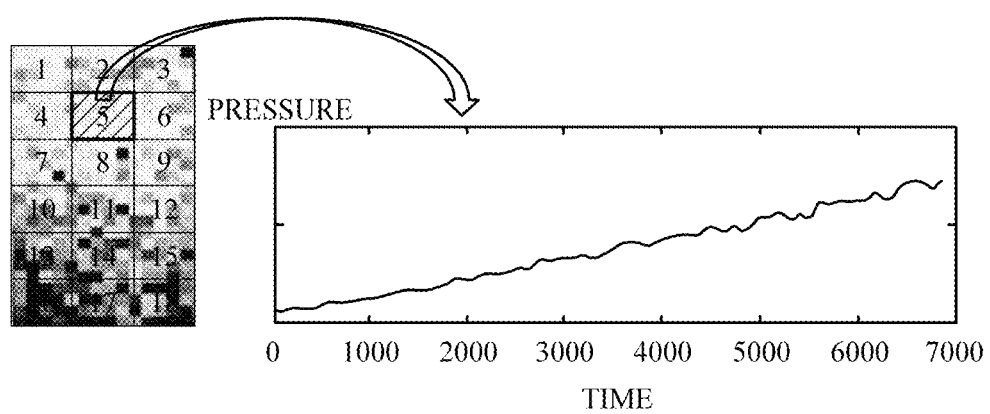

For example, FIG. 4B illustrates contact pressure distribution (1) obtained by the contact pressure sensor array 111 of the sensor part 110, and a contact image (2) obtained by the image sensor 113. FIG. 4C illustrates an example of obtaining a contact pressure signal by using contact pressure distribution. As illustrated in FIGS. 4A-4C, in the case where the region of interest selector 340 selects a fifth region of a contact image as a region of interest, and there is one contact pressure sensor in the fifth region, contact pressure values output by the contact pressure sensor at each time may be obtained as contact pressure for estimating bio-information. In the case where there are a plurality of contact pressure sensors in the fifth region, a total sum, a mean value, a maximum value, and/or a minimum value of contact pressure values of the plurality of contact pressure sensors, or a value calculated by using a pre-defined function of the contact pressure values of the plurality of contact pressure sensors, may be obtained as contact pressure for estimating bio-information.

Figure 4D:
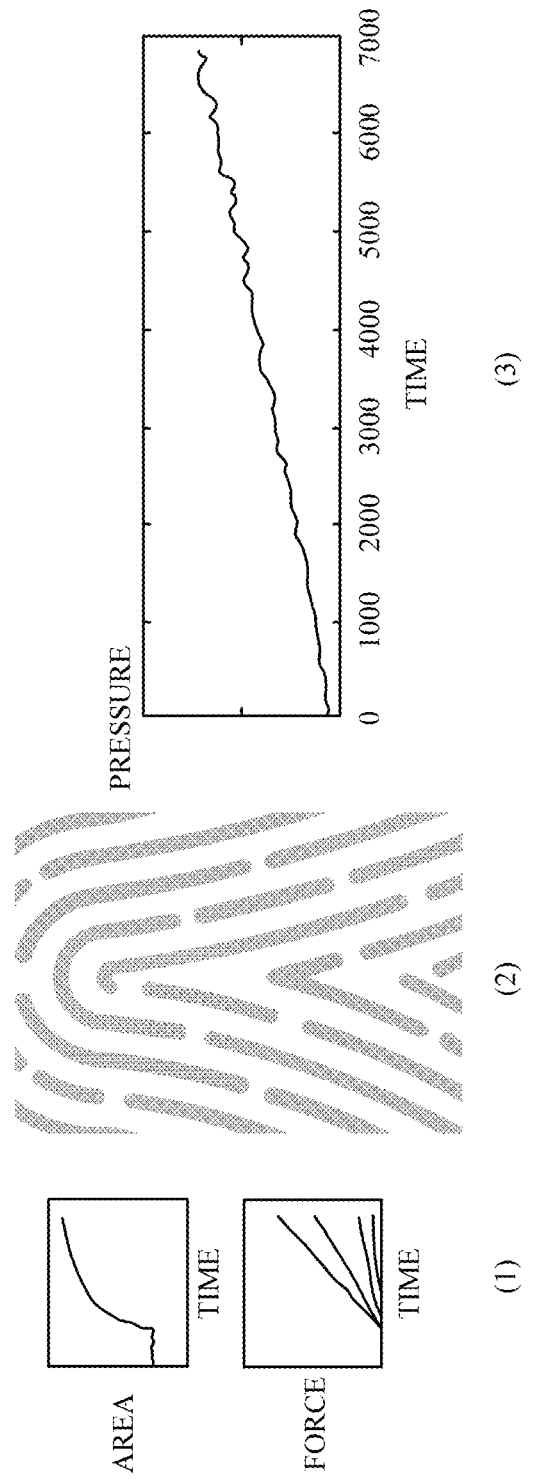

In another example, (1) of FIG. 4D illustrates a contact area and a contact force respectively obtained by the image sensor 113 and the force sensor 114 in the sensor part 110 of FIG. 2B; (2) of FIG. 4D illustrates a contact image obtained by the image sensor 113; and (3) of FIG. 4D illustrates an example where the contact pressure obtainer 320 obtains contact pressure by using the contact force and the contact area. As illustrated in FIG. 4D, when a user presses a contact surface with a finger while gradually increasing intensity, a contact force and a contact area are generally increased according to passage of time. As described above, the contact pressure obtainer 320 may obtain contact pressure using the obtained contact force and contact area.

In the case where the image sensor 113 has no separate area sensor, the contact pressure obtainer 120 may obtain a value, equivalent to a contact area, by using contact image data, e.g., pixel values output from each pixel of the image sensor 113. For example, the contact pressure obtainer 120 may convert a difference between statistical values (e.g., a total sum, a mean value, etc.) of pixel values of an entire region or a specific region at a first time and a second time of the measurement time period into a value equivalent to a contact area by applying a pre-defined area conversion function. However, this is merely an example and the method of determining a contact area is not limited thereto.

The region of interest selector 340 may divide a contact image into one or more regions, and may select a region of interest for estimating bio-information from among the regions. For example, the region of interest selector 340 may detect a position of a pre-defined characteristic point by analyzing the contact image, and may select a region, including the characteristic point, as a region of interest. For example, in the case where an object is a finger, the characteristic point may include a fingerprint center point.

In another example, once the pulse wave signal obtainer 310 obtains a pulse wave signal of each region, the region of interest selector 340 may evaluate a quality of a pulse wave signal of each region, and may select a region of interest based on a result of the evaluation. For example, the region of interest selector may select a region of interest corresponding to the highest quality of a pulse wave signal or a region of interest corresponding to a quality of a pulse wave signal of a certain value or greater. For example, the region of interest selector 340 may evaluate a pulse wave signal quality of each region based on a maximum amplitude value of a pulse wave signal of each region, a difference between a maximum amplitude value and a minimum amplitude value, an average amplitude value, and the like. However, this is merely an example, and the evaluation is not limited thereto. For example, the region of interest selector 340 may select a region, having the largest difference between a maximum amplitude value and a minimum amplitude value of a pulse wave signal, as a region of interest.

Upon receiving a request for estimating bio-information, the contact state guide part 350 may provide guide information on a reference contact pressure to be applied by a user to the sensor part 110. For example, the contact state guide part 350 may generate guide information including a reference contact pressure value at each measurement time and/or a change graph of the reference contact pressure during the entire measurement time period, and may output the generated guide information through an output part which will be described later. In an example embodiment, the guide information may include information for inducing a user to press the sensor part 110 with gradually increasing force for a predetermined period of time while the user touches the sensor part 110 with an object. In an alternative embodiment, the guide information may include information for inducing a user to press the sensor part 110 with gradually decreasing force in a state in which the user presses the sensor part 110 with a pressure greater than or equal to a threshold. However, these are merely examples and the disclosure is not limited thereto.

Further, once the contact pressure obtainer 320 obtains an actual contact pressure applied by a user to the sensor part 110 at each measurement time, the contact state guide part 350 may guide a user to maintain a contact intensity equal to or approximate to a reference contact pressure by using the actual contact pressure. In an example embodiment, the contact state guide part 350 may generate a graph showing a change in the reference contact pressure and a change in the actual contact pressure, and may output the generated graph through an output part, so that a user may visually recognize a difference between the reference contact pressure and the actual contact pressure.

In addition, the contact state guide part 350 may determine a contact state based on a contact image. For example, in the case where a pre-defined characteristic point is not included in a contact image, or a characteristic point is outside a predetermined region based on a specific point (e.g., center of an image) of the contact image, the contact state guide part 350 may determine that a contact state is not normal, and may guide a user to re-contact the sensor part 110 with an object.

Further, the contact state guide part 350 may determine a contact state based on a pulse wave signal of a region of interest. In response to determining that a pulse wave signal quality of a region of interest selected by the region of interest selector 340 does not satisfy one or more pre-determined criteria, the contact state guide part 350 may determine that a contact state is not normal. For example, in response to a difference between a maximum amplitude value and a minimum amplitude value of a pulse wave signal of a region of interest being lower than or equal to a threshold, the contact state guide part 350 may determine that a contact state is not normal. However, the determination of the contact state is not limited thereto.

The estimator 330 may estimate bio-information by using the pulse wave signal of the region of interest which is obtained by the pulse wave signal obtainer 310, and the contact pressure obtained by the contact pressure obtainer 320. For example, referring to FIGS. 4E and 4F, the estimator 330 may estimate blood pressure using oscillometry based on the pulse wave signal and the contact pressure.

Figure 4E:
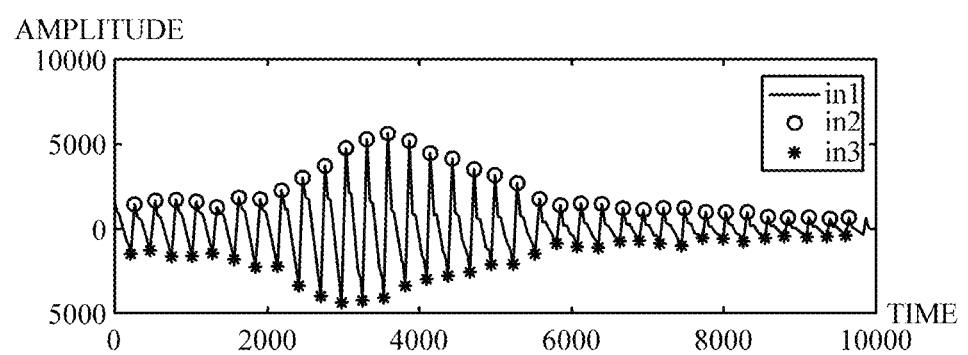

Referring to FIG. 4E, the estimator 330 may obtain an oscillometric envelope OW which represents a contact pressure versus pulse wave amplitude. The estimator 330 may extract a peak-to-peak point by subtracting an amplitude value in3 of a negative (−) point from an amplitude value in2 of a positive (+) point of a waveform envelope in1 at each measurement time of a pulse wave signal, and may obtain an oscillometric envelope OW by plotting a peak-to-peak amplitude at each measurement time based on a contact pressure value at the same measurement time of the peak-to-peak amplitude.

Figure 4F:
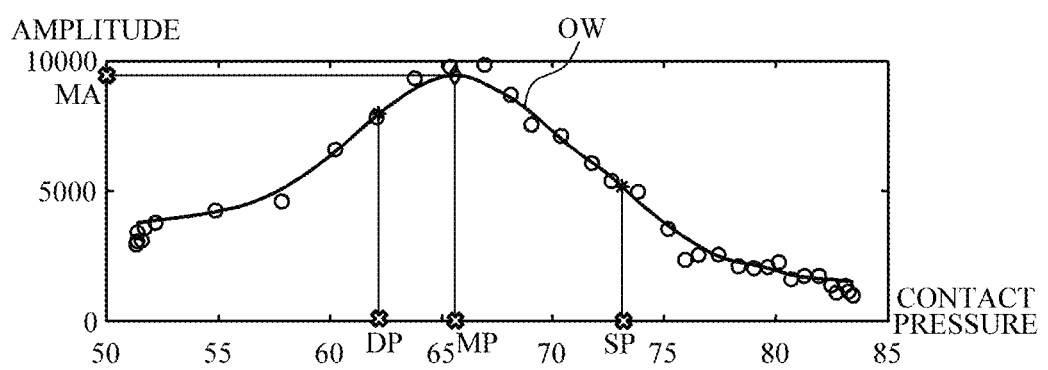

Referring to FIG. 4F, the estimator 330 may obtain feature values for estimating blood pressure from the obtained oscillometric envelope OW. The estimator 330 may obtain, as the feature values, an amplitude value MA and a contact pressure value MP of a maximum peak point, contact pressure values SP and DP located to the left and right of the contact pressure value MP of the maximum peak point and having a predetermined ratio (e.g., 0.5 to 0.7) to the contact pressure value MP, and the like.

Upon extracting the feature values, the estimator 330 may estimate bio-information by applying a pre-defined bio-information estimation model. In this case, the bio-information estimation model may be defined as various linear and/or non-linear combination functions, such as addition, subtraction, division, multiplication, logarithmic value, regression equation, and the like, with no specific limitation. For example, the following Equation 1 represents a simple linear equation.

$$y=ax+b \qquad \text{[Equation 1]}$$

Herein, y denotes a bio-information estimation value to be obtained; x denotes the extracted feature value; and a and b denote pre-calculated values obtained through preprocessing, and may be defined differently according to the types of bio-information to be obtained and user characteristics. For example, the estimator 330 may independently obtain mean arterial pressure (MAP), diastolic blood pressure (DBP), and systolic blood pressure (SBP) by using the above Equation 1 which is defined for each of the MAP, the DBP, and the SBP. For example, the estimator 330 may obtain the MAP, the DBP, and the SBP by inputting the extracted feature values MP, DP, and SP into a function defined for each of the values.

Referring back to FIG. 1B, the bio-information estimating apparatus 100b may further include the output part 130, the memory 140, and the communicator 150.

The output part 130 may output results processed by the sensor part 110 and the processor 120. For example, the output part 130 may visually output an estimated bio-information value and/or guide information by using a display module (e.g., a display device), or may output the information in a non-visual manner through voice, vibrations, tactile sensation, and the like, by using a speaker module (e.g., a speaker), a haptic module (e.g., a vibration motor), and the like. The output part 130 may divide a display area into two or more areas according to a setting, in which the output part 130 may output the pulse wave signal, the contact force, the contact area, and the like, which are used for estimating bio-information, in various forms of graphs in a first area; and may output an estimated bio-information value in a second area. In an example embodiment, in response to an estimated bio-information value falling outside a normal range, the output part 130 may output warning information in various manners, such as highlighting an abnormal value in red and the like, displaying the abnormal value along with a normal range, outputting a voice warning message, adjusting a vibration intensity, and the like.

The memory 140 may store processing results of the sensor part 110 and the processor 120. Further, the memory 140 may store various criteria for estimating bio-information. For example, the criteria may include user feature information such as a user's age, gender, health condition, and the like. In addition, the criteria may include various types of information, such as a bio-information estimation model, bio-information estimation criteria, a reference contact pressure, and the like, but are not limited thereto.

In this case, the memory 140 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communicator 150 may communicate with an external device 170 by using wired or wireless communication techniques under the control of the processor 120, and may transmit and receive various data to and from the external device. For example, the communicator 150 may transmit an estimation result of bio-information to the external device 170, and may receive various criteria for estimating bio-information from the external device 170. In an example embodiment, examples of the external device 170 may include a cuff-type blood pressure measuring device, and an information processing device such as a smartphone, a tablet PC, a desktop computer, a laptop computer, and the like.

In an example embodiment, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, these are merely examples and are not intended to be limiting.

Figure 5:
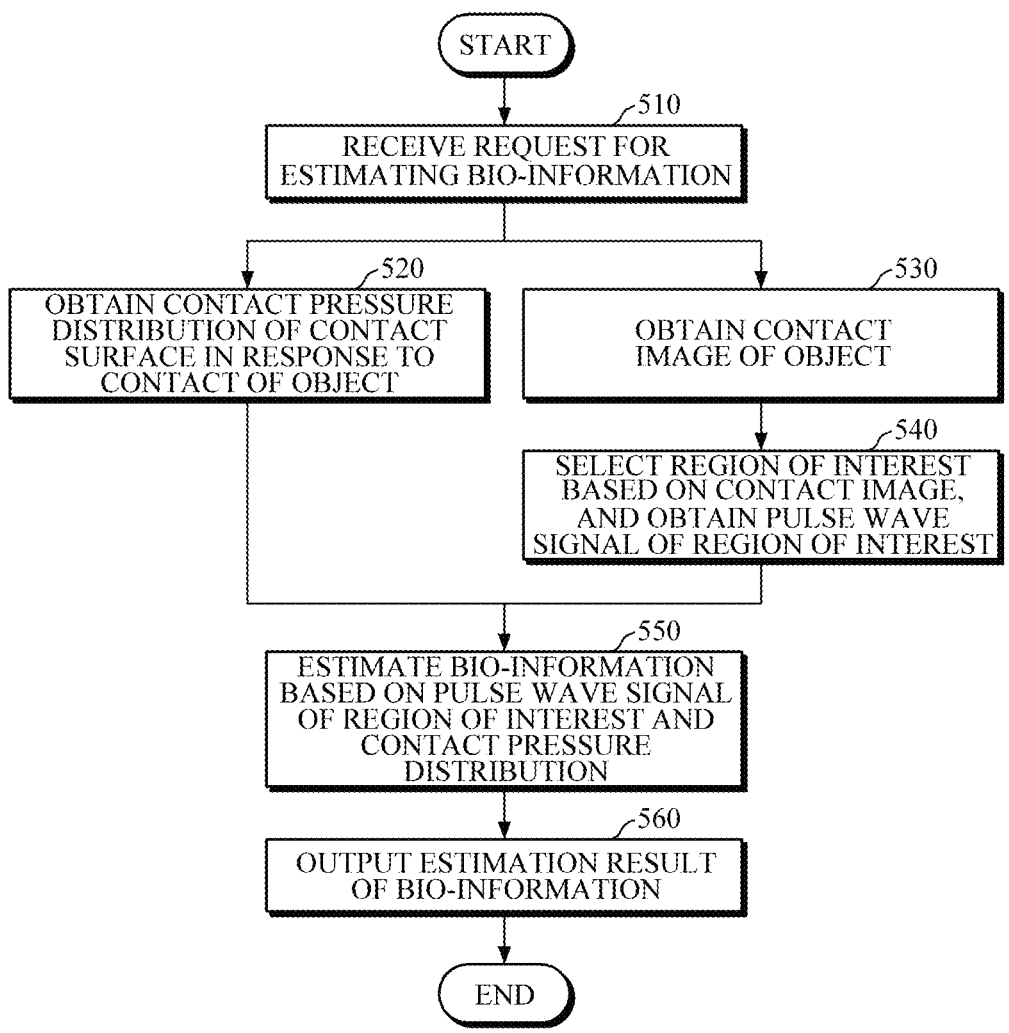
FIG. 5 is a flowchart illustrating a method of estimating bio-information according to an example embodiment.

FIG. 5 is a flowchart illustrating a method of estimating bio-information according to an example embodiment. The method of estimating bio-information of FIG. 5 may be an example of a bio-information estimating method performed by one or more of the bio-information estimating apparatuses 100a and 100b.

The bio-information estimating apparatus may receive a request for estimating bio-information in 510. The request for estimating bio-information may be received from a user or an external device which is connected to the bio-information estimating apparatus through communication. However, the request for estimating bio-information is not limited thereto, and it may be determined automatically (that is, without a user input) at predetermined intervals that the request for estimating bio-information is received. In this case, upon receiving the request for estimating bio-information, the bio-information estimating apparatus may provide guide information on a reference contact pressure to be applied by a user's object to the sensor part.

In response to contact of an object, the bio-information estimating apparatus may obtain contact pressure distribution and a contact image of the object for a predetermined period of time in 520 and 530. In this case, the user may change contact pressure by pressing the sensor part with, for example, a finger with gradually increasing force; or by pressing the sensor part with gradually decreasing force at a state in which the user contacts the sensor part with the finger with a pressure equal to or greater than a predetermined threshold. Alternatively, the bio-information estimating apparatus may change contact pressure by using various other methods such as touching the object from an external force.

Subsequently, the bio-information estimating apparatus may select a region of interest based on the contact image, and may obtain a pulse wave signal of the selected region of interest in 540. For example, the bio-information estimating apparatus may divide the contact image into one or more regions, and may select a region of interest from among the regions. For example, the bio-information estimating apparatus may detect a position of a pre-defined characteristic point in the contact image, and may select a region, including the detected position of the characteristic point, as a region of interest. In another example, the bio-information estimating apparatus may obtain a pulse wave signal in each region of the contact image, and may select a region of interest based on a pulse wave signal quality of each region. For example, the region of interest selector may evaluate a pulse wave signal quality of each region based on a maximum amplitude value of a pulse wave signal of each region, a difference between a maximum amplitude value and a minimum amplitude value, an average amplitude value, and the like. However, these are merely examples, and the evaluation is not limited thereto.

Next, the bio-information estimating apparatus may estimate bio-information based on the pulse wave signal of the region of interest and the contact pressure distribution in 550. For example, the bio-information estimating apparatus may estimate bio-information using oscillometry based on contact pressure at a position corresponding to the region of interest and a pulse wave signal of the region of interest.

Next, the bio-information estimating apparatus may output an estimation result of bio-information in 560. In this case, the bio-information estimating apparatus may output the estimation result of bio-information using various output devices, such as a display module for visual output, a speaker module for voice output, a haptic module for tactile output through vibration, tactile sensation, and the like.

Figure 6:
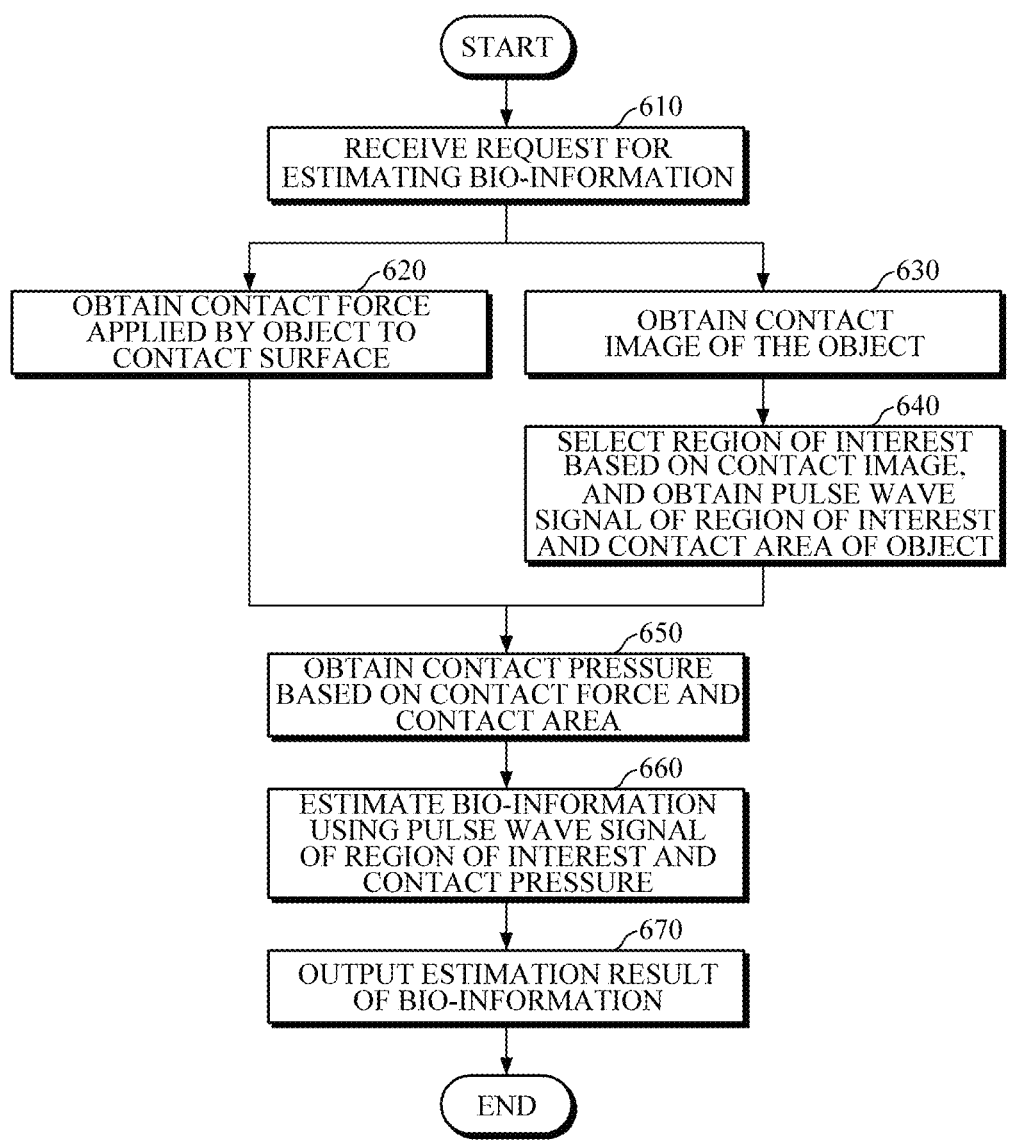
FIG. 6 is a flowchart illustrating a method of estimating bio-information according to an example embodiment.

FIG. 6 is a flowchart illustrating a method of estimating bio-information according to an example embodiment. The method of estimating bio-information of FIG. 6 may be an example of a bio-information estimating method performed by one or more of the bio-information estimating apparatuses 100a and 100b having the sensor part structure of FIG. 2B.

The bio-information estimating apparatus may receive a request for estimating bio-information in 610. When an object contacts a contact surface, the bio-information estimating apparatus may obtain a contact force applied by the object to the contact surface, and a contact image of the object in 620 and 630.

Next, the bio-information estimating apparatus may select a region of interest based on the contact image, and may obtain a pulse wave signal of the selected region of interest and a contact area of the object in 640. For example, the bio-information estimating apparatus may select a region of interest from among a plurality of regions, divided from the contact image, based on a region including a position of a characteristic point and/or a pulse wave signal quality of each area.

Subsequently, the bio-information estimating apparatus may obtain contact pressure based on the contact force and the contact area in 650, and may estimate bio-information by using the pulse wave signal of the region of interest and the contact pressure in 660.

Next, the bio-information estimating apparatus may output an estimation result of bio-information in 670. In this case, the bio-information estimating apparatus may output the estimation result of bio-information using various output devices, e.g., a display module for visual output, a speaker module for voice output, a haptic module for tactile output through vibration, tactile sensation, and the like.

Figure 7:
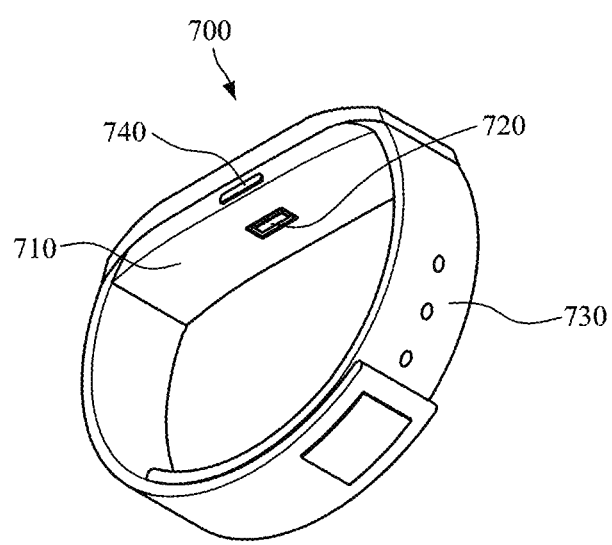
FIG. 7 is a diagram illustrating a wearable device, to which an apparatus for estimating bio-information according to an example embodiment is applied.

FIG. 7 is a diagram illustrating a wearable device, to which one or more example embodiments of an apparatus for estimating bio-information are applied. Various embodiments of the apparatus for estimating bio-information described above may be mounted in a smart watch worn on a wrist or a smart hand-type wearable device as illustrated in FIG. 7. However, the wearable device is merely an example for convenience of explanation, and it should not be construed that application of the embodiments is limited to a smart watch or a smart band-type wearable device.

Referring to FIG. 7, the wearable device 700 includes a main body 710 and a strap 730.

The strap 730 may be flexible, and may be connected to both ends of the main body 710 to be bent around a user's wrist or m ay be bent in a manner which allows the strap 730 to be detached from a user's wrist. Alternatively, the strap 730 may be provided as a band shape that is not separable. In this case, air may be injected into the strap 730 or an airbag may be included in the strap 730, so that the strap 730 may have elasticity according to a change in pressure applied to the wrist, and the change in pressure of the wrist may be transmitted to the main body 710.

A battery, which supplies power to the wearable device 700, may be embedded in the main body 710 or the strap 730.

Further, the main body 710 includes a sensor part 720 mounted on one side thereof. The sensor part 720 may be provided in any one of the structures of FIGS. 2A and 2B described above. For example, as illustrated in FIG. 7, the sensor part 720 may be mounted on a rear surface of the main body 810, so that the sensor part 720 may detect a bio-signal from blood vessel tissues of the upper portion of the wrist. In this case, a user may change contact pressure between the wrist and the sensor part 720, for example, by pressing a display, mounted on a front surface of the main body 710, with gradually increasing force with a finger of a hand while wearing the main body 710 on a wrist of the other hand, or by changing a thickness of the wrist by making hand movements, e.g., slowly opening the hand after clenching the first while wearing the main body 710 on the wrist. In another example, the sensor part 720 may be mounted on a front surface of the main body 710, so that while the user touches the sensor part 720 with a finger, the sensor part 720 may detect a bio-signal from the finger. In this case, a display panel of the sensor part 720 may perform a display function of displaying information to the user.

Further, the main body 710 may include a processor which controls various functions of the wearable device 700 including the sensor part 720, and estimates bio-information of an object (e.g., a user that wears the wearable device 700). In response to a user's request for estimating bio-information, the processor may generate a control signal to control the sensor part 720. The processor may estimate bio-information based on oscillometry using data obtained by the sensor part 720. Upon receiving the request for estimating bio-information from a user, the processor may provide the user with guide information on contact pressure (e.g., intensity, duration, etc.) between the sensor part 720 and the object through a display.

In an example embodiment, the display may be mounted on a front surface of the main body 710, and may visually output guide information on contact pressure and/or an estimation result of bio-information.

A memory may be mounted in the main body 710, and may store various types of information processed by the processor, and various criteria for estimating bio-information.

Further, the wearable device 700 may include a manipulator 740 which receives a control command of a user and transmits the received control command to the processor. The manipulator 740 may be mounted on a side surface of the main body 710, and may include a function for inputting a command to turn on/off the wearable device 700.

Moreover, the wearable device 700 may include a communicator for transmitting and receiving various data to and from an external device, and various other modules for performing additional functions provided by the wearable device 700.

Figure 8:
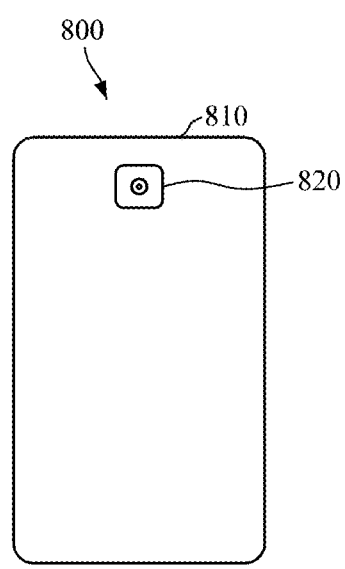
FIG. 8 is a diagram illustrating a smart device, to which an apparatus for estimating bio-information according to an example embodiment is applied.

FIG. 8 is a diagram illustrating smart device, to which one or more example embodiments of an apparatus for estimating bio-information are applied. In an example embodiment, the smart device may be a smartphone, a tablet PC, and the like.

Referring to FIG. 8, the smart device 800 includes a main body 810 and a sensor part 820 mounted the grain body 810. As illustrated in FIG. 8, the sensor part 820 may be mounted on a rear surface of the main body 810, so that the sensor part 820 may also perform the function of a front camera of the smart device 800. Alternatively, the sensor part 820 may be mounted in a fingerprint sensor area on a front surface of the main body 810, so that the sensor part 820 may also perform the function of a fingerprint sensor. In addition, the sensor part 820 may be mounted in a display area on the front surface of the main body 810, so that the display panel may perform the function of a display.

In addition, a display may be mounted on a front surface of the main body 810. The display may visually display an estimation result of bio-information and the like. The display may include a touch panel, and may receive various types of information input through the touch panel and transmit the received information to the processor.

Various other modules for performing example embodiments of the apparatuses and methods for estimating bio-information may be mounted in the smart device 800, and detailed description thereof will be omitted.

The example embodiments may be implemented as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g. data transmission through the Internet). The computer-readable recording medium can be distributed over a plurality of computer systems connected to a network so that a computer-readable code is written thereto and executed therefrom in a decentralized manner. Functional programs, codes, and code segments for implementing h example embodiments can be easily deduced by one of ordinary skill in the art.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

While a few example embodiments have been described above, the scope of the disclosure is not limited thereto and various modifications and improvements made by those of ordinary skill in the art to concepts defined in the following claims should be understood to fall within the scope of the disclosure.

What is claimed is:

1. An apparatus for estimating bio-information, the apparatus comprising:
    a sensor part comprising a contact pressure sensor array configured to obtain a contact pressure distribution of a contact pressure on a contact surface contacted by an object during a measurement period, and an image sensor configured to obtain a contact image of the object that contacts the contact surface at each measurement time in the measurement period; and
    a processor configured to:
        obtain a pulse wave signal of a region of interest based on the contact image, wherein amplitudes of the pulse wave signal of the region of interest at each measurement time are determined by using pixel values of the region of interest corresponding to each measurement time;
        obtain a contact pressure of the region of interest based on the contact pressure distribution;
        extract a peak-to-peak amplitude of each measurement time, by subtracting an amplitude value of a negative (−) point from an amplitude value of a positive (+) point of a waveform envelope of the pulse wave signal corresponding to each measurement time;
        obtain an oscillometric envelope by plotting the extracted peak-to-peak amplitude of the pulse wave signal of the region of interest based on a contact pressure at a same measurement time of the peak-to-peak amplitude;
        obtain at least one feature value based on the oscillometric envelope; and
        estimate the bio-information by using the at least one feature value.

2. The apparatus of claim 1, wherein the sensor part further comprises a display panel provided between the contact pressure sensor array and the image sensor.

3. The apparatus of claim 2, wherein the image sensor is further configured to detect light which is emitted from the display panel and is reflected or scattered from the object.

4. The apparatus of claim 1, wherein the contact pressure sensor array comprises a light-transmitting material.

5. The apparatus of claim 1, wherein the processor is further configured to divide the contact image into one or more regions, and select the region of interest based on at least one of a region, of the one or more regions, including a characteristic point in the contact image, and a quality of a pulse wave signal of each of the one or more regions.

6. The apparatus of claim 5, wherein the characteristic point comprises a fingerprint center point of a finger.

7. The apparatus of claim 5, wherein the processor is further configured to evaluate the quality of the pulse wave signal of each of the one or more regions based on at least one of a maximum amplitude value of the pulse wave signal of each of the one or more regions, a difference between the maximum amplitude value and a minimum amplitude value of the pulse wave signal of each of the one or more regions, and an average amplitude value of the pulse wave signal of each of the one or more regions.

8. The apparatus of claim 5, wherein the processor is further configured to obtain at least one of a total sum, a mean value, a median value, a maximum value, and a minimum value of image data measured at each measurement time in each of the one or more regions, and a value calculated by applying a pre-defined function to the image data measured at each measurement time in each of the one or more regions, as an amplitude component of the pulse wave signal of each of the one or more regions.

9. The apparatus of claim 1, wherein the processor is further configured to divide the contact image into one or more regions, and select the region of interest based on a contact pressure at a position corresponding to each of the one or more regions in the contact pressure distribution.

10. The apparatus of claim 1, wherein the at least one feature value comprises one or more of a first contact pressure value of a maximum amplitude point, a second contact pressure value located to a left of the first contact pressure value, and a third contact pressure value located to a right of the first contact pressure value, the second contact pressure value and the third contact pressure value having a predetermined ratio to the first contact pressure value of the maximum amplitude point, in the oscillometric envelope.

11. The apparatus of claim 1, wherein the processor is further configured to determine a contact state between the object and the sensor part based on at least one of the contact pressure distribution, the contact image, and the pulse wave signal of the region of interest.

12. The apparatus of claim 11, further comprising an output circuitry configured to output information on the contact state.

13. The apparatus of claim 1, wherein the bio-information comprises one or more of blood pressure, vascular age, arterial stiffness, aortic pressure waveform, vascular compliance, stress index, degree of fatigue, skin elasticity, and skin age.

14. A method of estimating bio-information, the method comprising:
    obtaining, by using a contact pressure sensor array, a contact pressure distribution of a contact pressure on a contact surface contacted by an object during a measurement period;
    obtaining, by using an image sensor, a contact image of the object that contacts the contact surface at each measurement time in the measurement period;
    obtaining a pulse wave signal of a region of interest based on the contact image, wherein amplitudes of the pulse wave signal of the region of interest at each measurement time are determined by using pixel values of the region of interest corresponding to each measurement time;
    obtaining a contact pressure of the region of interest based on the contact pressure distribution;
    extracting a peak-to-peak amplitude of each measurement time, by subtracting an amplitude value of a negative (−) point from an amplitude value of a positive (+) point of a waveform envelope of the pulse wave signal corresponding to each measurement time;
    obtaining an oscillometric envelope by plotting the extracted peak-to-peak amplitude of the pulse wave signal of the region of interest based on a contact pressure at a same measurement time of the peak-to-peak amplitude;

obtaining at least one feature value based on the oscillometric envelope; and estimating the bio-information by using the at least one feature value.

15. The method of claim 14, wherein the obtaining the pulse wave signal of the region of interest comprises:

dividing the contact image into one or more regions; and selecting the region of interest based on at least one of a region, of the one or more regions, including a characteristic point in the contact image, and quality of a pulse wave signal of each of the one or more regions.

16. The method of claim 15, wherein the selecting comprises evaluating the quality of the pulse wave signal of each of the one or more regions based on at least one of a maximum amplitude value of the pulse wave signal of each of the one or more regions, a difference between the maximum amplitude value and a minimum amplitude value of the pulse wave signal of each of the one or more regions, and an average amplitude value of the pulse wave signal of each of the one or more regions.

17. The method of claim 14, wherein the obtaining the pulse wave signal of the region of interest comprises:

dividing the contact image into one or more regions; and selecting the region of interest based on a contact pressure at a position corresponding to each of the one or more regions in the contact pressure distribution.

* * * * *